US008017396B2

(12) United States Patent
Kumar

(10) Patent No.: US 8,017,396 B2
(45) Date of Patent: Sep. 13, 2011

(54) CELLULOSE BASED HEART VALVE PROSTHESIS

(76) Inventor: Vijay Kumar, Coralville, IA (US)

( * ) Notice: Subject to any disclaimer, the term of this patent is extended or adjusted under 35 U.S.C. 154(b) by 4 days.

(21) Appl. No.: 12/391,249

(22) Filed: Feb. 23, 2009

(65) Prior Publication Data

US 2009/0222085 A1 Sep. 3, 2009

Related U.S. Application Data

(60) Provisional application No. 61/030,935, filed on Feb. 22, 2008.

(51) Int. Cl.
*B05D 3/00* (2006.01)
*C12N 5/00* (2006.01)

(52) U.S. Cl. ..... 435/402; 623/1.26; 623/2.18; 623/2.42; 427/2.24

(58) Field of Classification Search .................. None
See application file for complete search history.

(56) References Cited

U.S. PATENT DOCUMENTS

| | | | |
|---|---|---|---|
| 4,753,652 | A | 6/1988 | Langer |
| 5,679,112 | A | 10/1997 | Levy et al. |
| 5,986,168 | A | 11/1999 | Noishiki |
| 6,254,635 | B1 | 7/2001 | Schroeder et al. |
| 6,436,091 | B1 | 8/2002 | Harper |
| 6,627,749 | B1 | 9/2003 | Kumar |
| 6,800,753 | B2 | 10/2004 | Kumar |
| 6,821,531 | B2 | 11/2004 | Kumar |
| 7,166,464 | B2 | 1/2007 | McAllister et al. |
| 2001/0025196 | A1 | 9/2001 | Chinn et al. |
| 2002/0086990 | A1 | 7/2002 | Kumar et al. |
| 2003/0083741 | A1 | 5/2003 | Woo |
| 2004/0047909 | A1 | 3/2004 | Ragheb |
| 2004/0115273 | A1 | 6/2004 | Sparer et al. |
| 2004/0219185 | A1 | 11/2004 | Ringeisen |
| 2005/0064038 | A1 | 3/2005 | Dinh |
| 2005/0131225 | A1 | 6/2005 | Kumar et al. |
| 2005/0143807 | A1 | 6/2005 | Pavcnik |
| 2005/0287208 | A1 | 12/2005 | Kumar et al. |
| 2006/0093672 | A1 | 5/2006 | Kumar et al. |
| 2006/0193885 | A1 | 8/2006 | Neethling |
| 2006/0265053 | A1 | 11/2006 | Hunt |
| 2007/0003588 | A1 | 1/2007 | Chinn |
| 2007/0038295 | A1 | 2/2007 | Case |
| 2007/0203564 | A1 | 8/2007 | Rusk |
| 2007/0213801 | A1 | 9/2007 | Kutryk et al. |
| 2007/0275458 | A1 | 11/2007 | Gouma |

OTHER PUBLICATIONS

Kim, Y.J., et al., Fluorometric Assay of DNA in Cartilage Explants Using Hoechst 33258, Anal Biochem (1988) 174: 168-176.
Hoerstrup et al., Functional Living Trileaflet Heart Valves Grown in Vitro, Circulation, (2000) 102(19): 44-49.
Farndale et al., Improved quantitation and discrimination of sulphated glycosaminoglycans by use of dimethylmethylene blue, Biochim Biophys Acta, (1986) 883: 173-177.
G. H. M. Engbers, et al., Blood compatible hemodialysis membranes, Trans. Annual meeting of the Society for Biomaterials and the International Biomaterials Symposium, (1994) p. 109.
J. Morales et al., Plasma modification of cellulose fibers for composite materials, J. Appl. Polym. Sci., (2006); 101:3821-3826.
J. Zhang et al., Chemical modification of cellulose membranes with sulfoammonium zwitterionic vinyl monomer to improve hemocompatibility, Colloids and Surfaces B: Biointerfaces (2003) 30:249-257.
J. Yuan et al., Improvement of blood compatibility on cellulose membrane surface by grafting betaine, Colloids and Surfaces B: Biointerfaces (2003); 30:147-155.
Roy Chowdhury & Kumar, "Fabrication and Evaluation of Porous 2,3-Dialdehydecellulose Membrane as Potential Biodegradable Tissue-engineering Scaffold," J. Biomed. Mater. Res. (2006) 76A: 300-309.
Mol, A., et al., Autologous Human Tissue-Engineered Heart Valves: Prospects for Systemic Application, Circulation (2006), 114 (suppl 1): 1152-1158.
Thubrikar, M., et al., The Elastic Modulus of Canine Aortic Valves in Vivo and in Vitro, Circ Res. (1980), 47 (5):792-800.
Zioupos, P., et al., Changes in the mechanical properties of bioprosthetic valve leaflets made of bovine pericardium, as a result of long-term mechanical conditioning in vitro and implantation in vivo, J. Mater Sci: Mater Med. (1993), 4(6): 531-537.
Bernacca G. M., et al., Hydrodynamic function of polyurethane prosthetic heart valves: influences of Young's modulus and leaflet thickness, Biomaterials, (2002), 2391):45-50.
Huszar et al., Monitoring of Collagen and Collagen Fragments in Chromatography of Protein Mixtures, Anal Biochem, (1980) 105:424-429.
Chandran, K. B., et al., Pulsatile Flow Past Aortic Valve Bioprostheses in a Model Human Aorta, J Biotech, (1984) 17(8):609.
In Kap Ko and Hiroo Iwata, An Approach to Constructing Three-Dimensional Tissue, Annals New York Academy of Sciences, vol. 944 (2006) pp. 443-455.
Entcheva, Emilia, et al., Functional cardiac cell constructs on cellulose-based scaffolding, Biomaterials 25 (2004) pp. 5753-5762.
Sodian, Ralf, MD, et al., Tissue Engineering of Heart Valves: In Vitro Experiences; Ann Thorac Surg 2000; 70:140-44.
Sodian, Ralf, MD, et al., Fabrication of a Trileaflet Heart Valve Scaffold from a Polyhydroxyalkanoate Biopolyester for Use in Tissue Engineering, Tissue Engineering, vol. 6, No. 2, 2000, pp. 183-188. Millon, L.E and Wan, W.K., The Polyvinyl Alcohol-Bacterial Cellulose System as a New Nanocomposite for Biomedical Applications, J. Biomed Mater Res Part B: Appl Biomater, 79B: 245-253 (2006).
Backdahl, H., et al., Mechanical properties of bacterial cellulose and interactions with smooth muscle cells, Biomaterials 27 (2006) 2141-49.
Fries, C.C. and Wesolowski, S.A., The polyester-oxidized cellulose compound vascular prosthesis: A preliminary report, Trans. Amer. Soc. Artif. Int. Organs, vol. X (1964), 227-230.
Pulapura, S. and Kohn, J., Trends in the Development of Bioresorbable Polymers of Medical Applications, J. Biomaterials Applications, vol. 6, pp. 216-250 (1992).
Helenius, G. et al., In vivo biocompatibility of bacterial cellulose, J. Biomed Mater Res Part A, vol. 76A (2005), pp. 431-438.

*Primary Examiner* — Jim Ketter
(74) *Attorney, Agent, or Firm* — McDonnell Boehnen Hulbert & Berghoff LLP

(57) ABSTRACT

Disclosed are cellulose-based pliable, porous and non-porous prosthesis structures that can be formed to various geometries such as thin films, membranes, hollow tubes, heart valves, including an aortic heart valve. Also disclosed are methods for preparing a cellulose-based porous prosthesis structure.

12 Claims, 9 Drawing Sheets

(A)

(B)

(C)

(A)

(B)

(C)

(D)

CELLULOSE BASED HEART VALVE PROSTHESIS

This application claims priority to U.S. Provisional Patent Application Ser. No. 61/030,935, filed Feb. 22, 2008, and is incorporated herein by reference.

FIELD OF THE INVENTION

The invention relates generally to medical devices, and more particularly to a cellulose-based heart valve prosthesis, and methods for making such a heart valve prosthesis.

BACKGROUND OF THE INVENTION

The human heart consists of four valves, namely the mitral valve, tricuspid valve, pulmonary valve, and aortic valve, which can become damaged or diseased. According to statistics for 2005 published by the American Heart Association (AHA), valvular-related heart disease accounted for 20,891 mortalities (43,900 total mention mortalities), aortic valve disorder accounted for 13,137 mortalities (27,390 total mention mortalities), pulmonary valve disorder: accounted for 20 mortalities (45 total mention mortalities), mitral valve disorder accounted for 2,605 mortalities (6,210 total mention mortalities), tricuspid valve disorder accounted for 20 mortalities (114 total mention mortalities), and endocarditis accounted for 5,109 mortalities (10,120 total mention mortalities). Prosthetic heart valves have been used to replace such damaged or diseased heart valves. Of the four valves, the aortic valve experiences the largest day-to-day stress of any component of the heart, opening about 70 times a minute, or about 100,000 times a day. Accordingly, day-to-day stresses as well as additional stresses deriving from conditions or pathologies such as endocarditis, stenosis (restricted valve opening), or regurgitation (valve leakage), can ultimately accelerate improper valve function, particularly the aortic valve. If such conditions and stresses are left untreated, they can lead to heart failure. Currently, the end-stage treatment of dysfunctional heart valves, such as the aortic valve, involves replacement with a mechanical or a bioprosthetic device. While these mechanical and bioprosthetic heart valves have been used widely (the AHA estimates that 95,000 inpatient valve procedures were performed in 2003) they have certain disadvantages.

Mechanical valves are the most commonly and widely used prostheses. They are commonly made of titanium, cobalt-chromium alloy (Haynes 25), or pyrolytic carbon (Pyrolite). Compared to animal-derived heart valves, mechanical heart valves are more reliable and longer-lived (10-15 years with re-operation rates around 2-5%). Nevertheless, mechanical heart valves cause thrombus formation and calcification, which require that the patient maintains an anticoagulation therapeutic regimen for the rest of his or her life. Anticoagulation therapy has been linked to bleeding and other complications, such as damage of the red blood cells. It also predisposes the recipient to lifelong risks of infection.

Bioprosthetic valves are obtained from either animal origins (porcine valve or bovine pericardial valves) or human donors (cadavers). Animal-derived prostheses (stented and non-stented) use glutaraldehyde as a cross-linking agent, which enhances the mechanical stability of the prosthesis, but also fixes the protein configuration. This ultimately prevents cells in the prosthesis from growing, repairing and remodeling. Glutaraldehyde crosslinks have also been implicated as foci for calcification, which causes the prosthesis to deteriorate over time. Typically, bioprosthetic heart valve needs to be replaced within 5-15 years, depending on the age of the recipient. Immunologic reactions have also been noted with animal-based valve prosthesis, further limiting their use as a suitable substitute. The risk of transferring infectious diseases, such as zoonoses and Creutzfeldt-Jakob, to the patient also exists with the animal-derived prosthesis.

Human-derived aortic valves are obtained from cadavers. Although the aortic valve replacement with an allograft is ideal (because there is resistance to infection, no requirement for anticoagulation therapy, and surgical advantages) there are not enough human donors available. Cryopreserved pulmonary valves have been used to replace aortic valves but they can result in early failure. These valves also demonstrate gross regurgitation in vitro and are less robust against the hemodynamic stresses in the aortic position. Further, there is no consensus concerning the extent of cell viability within these human aortic valves.

Polymeric heart valves were first developed and sporadically used in clinics in 1950s but their use ceased soon thereafter because of high rates of thrombosis and thromboembolic complications and valve degeneration. However, in recent years, with the availability of new flexible polymers with improved biocompatibility, hemocompatibility and durability, polymer heart valves have regained considerable attention. Polyetherurethane, polyetherurethane urea, segmented polyurethanes, polycarbonate urethane, polyurethane valves coated with polyethylene oxide-grafted polyurethane, and polystyrene-b-polyisobutylene-polystyrene are among the polymers that show promise. The advantage of flexible polymer heart valves is that they can be fabricated into the native valve geometry and as a result they display normal hemodynamic function. The long term durability and hemodynamic function of these valves in vivo, however, remain to be proven. Thus, the search for a new material with improved performance continues.

Accordingly, there exists a need in the art for replacement heart valves that exhibit improved characteristics relative to existing mechanical and bioprosthetic heart valves.

SUMMARY OF THE INVENTION

In one aspect, the invention relates to a single-pieced, cellulose-based heart valve prosthesis comprising (a) a stent body; and (b) a plurality of leaflet-forming membranes, wherein (i) the stent body defines a generally tubular shape centered about an axis; and (ii) the plurality of leaflet-forming membranes are located within the stent body so as to form a one-way valve prosthesis, wherein the valve prosthesis comprises a proximal end and a distal end.

In another aspect, the invention provides a method for preparing a cellulose-based structure comprising: (a) providing a source of cellulose; (b) treating the cellulose with paraformaldehyde in anhydrous dimethylsulfoxide (DMSO) under conditions suitable to form methylolcellulose; (c) optionally mixing the methylolcellulose with a water-soluble porogen; (d) casting the methylolcellulose mixture or methylolcellulose and porogen mixture in a mold; (e) soaking the methylolcellulose and porogen in a DMSO-miscible organic solvent or a mixed solvent system (e.g., water/acetone; methanol-2-propanol (2:1)) in which methylolcellulose is not soluble under conditions suitable to form a solid methylolcellulose-porogen matrix; and (f) removing the matrix from the mold and soaking the solid matrix in water until the cellulose-based structure is formed. In embodiments of the above aspect when the method does not comprise (c) the soaking associated with (e) can also be optional in the method.

In yet another aspect, the invention provides a method for preparing a cellulose-based aortic heart valve prosthesis formed as a single unit comprising: (a) providing a source of cellulose; (b) treating the cellulose with paraformaldehyde in anhydrous dimethylsulfoxide (DMSO) under conditions suitable to form methylolcellulose; (c) optionally mixing the methylolcellulose with a water-soluble porogen; (d) casting the methylolcellulose mixture or methylolcellulose and porogen mixture in a mold having the general shape of an aortic heart valve; (e) soaking the methylolcellulose and porogen in a DMSO-miscible organic solvent or a mixed solvent system (e.g., water/acetone; methanol-2-propanol (2:1)) in which methylolcellulose is not soluble under conditions suitable to form a solid methylolcellulose-porogen matrix; and (f) removing the matrix from the mold and soaking the solid matrix in water until the cellulose-based aortic heart valve structure is formed. In embodiments of the above aspect when the method does not comprise (c) the soaking associated with (e) can also be optional in the method.

In another aspect, the invention provides a cellulose-based heart valve prosthesis that is produced by the process of the invention.

Other aspects of the invention will become apparent to those of skill in the art in view of the following detailed description.

DETAILED DESCRIPTION

Figure 1:
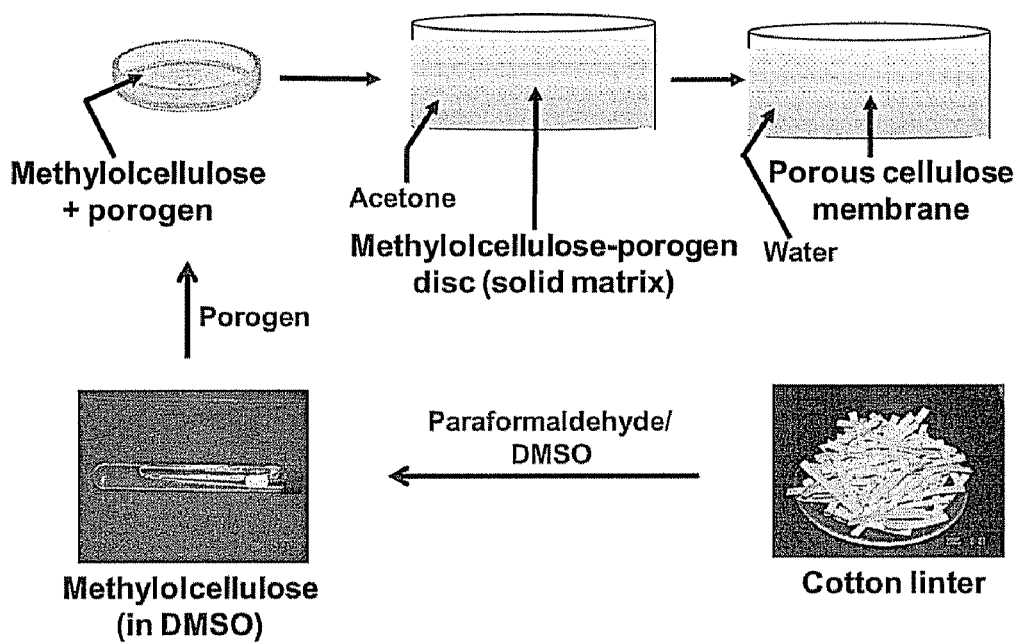
FIG. 1 depicts a general schematic diagram for one embodiment for generating a porous cellulose membrane from a starting cellulose material.

The invention provides cellulose-based pliable prosthesis structures. The prostheses can be made to conform to a variety of structures, including simple membranes, hollow tubes, heart valves, or combinations of those structures such as, for example, a stent-aortic heart valve prosthesis. The prosthesis structures can support cell adhesion and growth, and thus, can be used in a variety of surgical and/or implantation applications such as, for example, heart valve replacement surgery. The invention also provides methods for preparing a cellulose-based prosthesis structure comprising (a) providing a source of cellulose; (b) treating the cellulose with paraformaldehyde in anhydrous dimethylsulfoxide (DMSO) under conditions suitable to form methylolcellulose; (c) optionally mixing the methylolcellulose with a water-soluble porogen; (d) casting the methylolcellulose mixture or methylolcellulose and porogen mixture in a mold; (e) soaking the methylolcellulose and porogen in a DMSO-miscible organic solvent or a mixed solvent system (e.g., water/acetone; methanol-2-propanol (2:1)) in which methylolcellulose is not soluble under conditions suitable to form a solid methylolcellulose-porogen matrix; and (f) removing the matrix from the mold and soaking the solid matrix in water until the cellulose-based structure is formed. In embodiments of the above aspect when the method does not comprises (c) the soaking associated with (e) can also be optional in the method. The invention also relates to cellulose-based prosthesis produced by the methods of the invention.

Cellulose is a known natural biostable and biocompatible polymer material. Due to its abundance in nature and safe biological characteristics, cellulose has been used in a number of physiologically-related applications, such as wound healing; hemodialysis membranes; carriers for enzyme immobilization in biosensors; as coating and matrix materials for drugs; in hollow fiber perfusion systems; and as a substrate for cell growth and tissue regeneration. The invention described herein provides for cellulose-based prostheses in a variety of geometries such as, for example, heart valves (e.g., a valve and supporting stent) and blood vessels (hollow tubes). The invention also provides for a method that allows for simple modification of the physical characteristics of the resulting prosthesis, such as pore size, porosity, wall thickness, surface chemistries, and mechanical and hemodynamic properties. Thus, the porous cellulose-based prostheses (scaffolds) of the invention are highly versatile and uniquely suited to improve the design of effective cell-prosthesis (hybrid/bioengineered) composite-based implants, such as cardiovascular implants. Similarly, the cellulose-based prostheses of the invention can be designed to have low or no porosity for use as prostheses for direct implant into a patient. Such prostheses are designed to have no fluid leakage or intra-prosthesis permeation.

All publications, patent applications, patents and other references mentioned herein, if not otherwise indicated, are explicitly incorporated by reference herein their entirety for all purposes as if fully set forth.

Unless otherwise defined, all technical and scientific terms used herein have the same meaning as commonly understood by one of ordinary skill in the art to which this disclosure belongs. In case of conflict, the present specification, including definitions, will control.

When an amount, concentration, or other value or parameter is given as a range, or a list of upper and lower values, this to be understood as specifically disclosing all ranges formed from any pair of any upper and lower range limits, regardless of whether ranges are separately disclosed. Where a range of numerical values is recited herein, unless otherwise stated, the range is intended to include the endpoints thereof, and all integers and fractions within the range. It is not intended that the scope of the disclosure be limited to the specific values recited when defining a range.

When the term "about" is used in describing a value or an end-point of a range, the disclosure should be understood to include the specific value or end-point referred to.

The use of "a" or "an" to describe the various elements and components herein is merely for convenience and to give a general sense of the disclosure. This description should be read to include one or at least one and the singular also includes the plural unless it is obvious that it is meant otherwise.

Cellulose-based Prosthesis

Normal aortic valve function is based on structural integrity and coordinated interactions among the cusps, commissures, and the supporting structure in the aortic root. For engineering an aortic valve, a cellulose-based prosthesis can present cell adhesive sites with an interconnected porous structure for in-growth, provide the geometrical guidance to the attached cells, and be able to bear the stresses encountered in the aortic valve position. For the reasons described herein, cellulose-based compositions provide an excellent prosthesis material for applications that benefit from the use of materials that are biostable and biocompatible, and further, if desired, can be selectively digested in vitro to create tissue engineered constructs, such as a heart valve.

In one aspect, the invention provides a cellulose-based prosthesis in a variety of different geometries including, for example, porous membranes, hollow tubes, and heart valves. In one embodiment the cellulose-based prosthesis comprises a geometry having the shape of a heart valve, comprising a stent body, and one or a plurality of leaflet-forming membranes. The stent body defines a generally tubular shape centered about an axis. The one or more leaflet-forming membranes are located within the stent body and form a one-way valve such that the valve comprises an inflow (or proximal) end and an outflow (or distal) end. In an embodiment, the valve comprises a geometry based on any type of mammalian heart valve, such as one, two, or three leaflet-forming membranes. For certain embodiments, wherein the valve comprises two or more leaflet-forming membranes, each membrane typically has a free edge that extends inward from the stent body and coapts or meets the other free edge(s) of the other leaflet-forming membrane(s), typically along radial lines spaced 180 degrees or 120 degrees apart with respect to each other to close the valve during the back flow cycle of blood flow. When blood flows in the proper direction (e.g., from the inflow to the outflow end) the free edges of the membranes move radially outward away from each other toward the interior surface of the stent body, thereby opening the valve.

In certain embodiments, the invention provides cellulose-based porous prosthesis structures as well as cellulose-based porous scaffold structures. The term "porous" as used herein can encompass a range of pore sizes (e.g., micropores, mesopores, etc.), degree of pore interconnectivity, channel size, and the like. One of skill will be able to manipulate the pore size of the cellulose-based structures so that appropriate pore size is selected given the intended use of the structure. For example, in order to avoid excessive blood leakage or permeation, typically the pore size of a cellulose-based porous prosthesis will be smaller relative to a cellulose-based prosthesis/scaffold for use in generating a hybrid (e.g., cellulose-cell) or tissue engineered valve structure. As a non-limiting example a cellulose-based porous prosthesis can be produced wherein the porous structure is micro- or mesoporous by adding a methylolcellulose solution to an appropriate mold, and subsequently contacting the mold containing methylolcellulose with water.

In an embodiment the cellulose-based prosthesis further comprises at least one layer of cells. In an embodiment the at least one layer of cells comprises mammalian cells such as, for example myofibroblast cells or endothelial cells, or both. In other embodiments the at least one layer of cells comprises mammalian cells such as, for example, smooth muscle cells, fibroblast cells, progenitor or stem cells. In such embodiments the cellulose-based prosthesis can comprises a hybrid construct (a cellulose-cell matrix) wherein the cell comprises mammalian fibroblast cells integrated with the cellulose, and the luminal side, and/or the lining of the prosthesis comprises a layer of endothelial cells. In other embodiments, the cellulose-based prosthesis (or hybrid construct) can comprise a first layer of cells such as, for example, human myofibroblast cells, and a second layer of cells such as, for example, human endothelial cells. Further, the cellulose in such hybrid constructs can be selectively degraded by any compound, method, or biomolecule that degrades cellulose such as, for example, digestion by cellulase. Typically the cellulose digestion is performed while cell proliferation is occurring throughout the construct. However, cellulose digestion can be performed when substantially all the construct is covered by cells. The rate of digestion of the cellulose material and the rate of cellular proliferation can be controlled such that the amount of cellulose provides adequate support for cell proliferation and tissue growth. Thus, in one embodiment the cellulose-based prosthesis comprises a scaffold structure for cell growth in the shape of a heart valve for producing a tissue engineered heart valve. Accordingly, these constructs can be used for tissue engineering applications such as, for example, producing autologous tissue engineered heart valves or blood vessels, using techniques that are known in the art.

Figure 3:
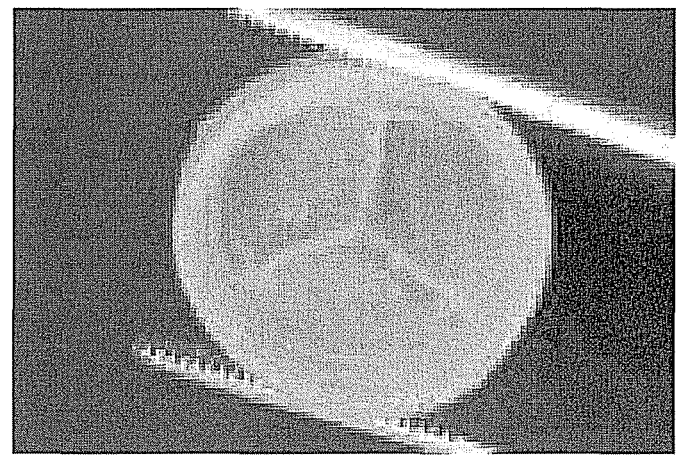
FIG. 3A depicts the distal view (outflow end) of an aortic heart valve prosthesis.
FIG. 3B depicts the proximal view (inflow end) of the aortic heart valve prosthesis.
FIG. 3C depicts the view of outer surface of the stent portion of the aortic heart valve prosthesis (19 mm diameter).
Figure 3:
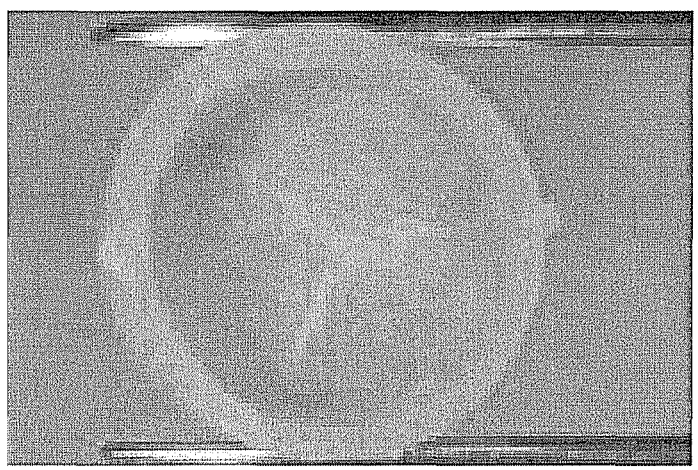
Figure 3:
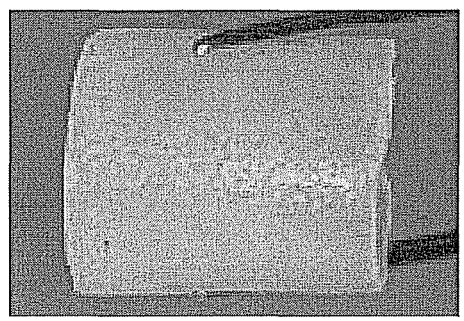

In one embodiment the cellulose-based prosthesis comprises a geometry having the size and shape of an aortic heart valve, comprising a stent body, and three leaflet-forming membranes, wherein stent body defines a generally tubular shape centered about an axis, and the three leaflet-forming membranes are located within the stent body, each leaflet having a free edge that extends inward from the stent body and abuts the free edge of the other two membranes along radial lines spaced about 120 degrees apart with respect to each other (see FIG. 3). In an embodiment, the stent body and the three leaflet-forming membranes are formed from a single piece of cellulose-based material.

In other embodiments, the cellulose-based prosthesis comprises a geometry having the size and shape of any type of heart valve having a trileaflet structure (e.g., pulmonary valve, tricuspid valve, etc.), comprising a stent body, and three leaflet-forming membranes, wherein stent body defines a generally tubular shape centered about an axis, and the three leaflet-forming membranes are located within the stent body, each leaflet having a free edge that extends inward from the stent body and abuts the free edge of the other two membranes along radial lines spaced about 120 degrees apart with respect to each other. In an embodiment, the stent body and the three leaflet-forming membranes are formed from a single piece of cellulose-based material.

In an embodiment, the cellulose-based prosthesis comprises a geometry having the size and shape of any type of heart valve having a bileaflet structure (e.g., mitral valve), comprising a stent body, and two leaflet-forming membranes, wherein stent body defines a generally tubular shape centered about an axis, and the two leaflet-forming membranes are located within the stent body, each leaflet having a free edge that extends inward from the stent body and abuts the free edge of the other two membranes along radial lines spaced about 180 degrees apart with respect to each other. In an embodiment, the stent body and the two leaflet-forming membranes are formed from a single piece of cellulose-based material.

In another embodiment the cellulose-based prosthesis comprises a geometry having the general shape of a hollow tube. In one embodiment, the hollow tube shaped prosthesis comprises a diameter appropriate for a vascular graft prosthesis.

The cellulose-based prostheses and scaffolds described herein find wide use in many applications that are treated through introduction of prosthetic or tissue engineered structures. For example, an adult subject suffering from a defective heart valve can benefit from a cellulose based heart valve prosthesis as described herein. While a young subject (child) suffering from a defective heart valve can also benefit from a cellulose-based hearth valve prosthesis, a tissue engineered heart valve may be particularly advantageous because such a heart valve will grow along with child as the child becomes an adult. Thus, the prostheses and scaffolds described herein can be used to treat patients affected by a wide range of disorders such as, for example, congenital heart defects (bicuspid aortic valve); faulty, failing or diseased heart valves; vascular diseases (intraluminal grafts, replacement or bypass of diseased or damaged blood vessels), and the like.

In yet another embodiment, the cellulose-based prosthesis can comprise any number of surface modification chemistries that are known in the art to improve hemocompatibility and cellular adhesive properties, such as, for example, fatty acids, hyaluronic acid, polyoxyethylene, sulfoammonium zwitterionic vinyl monomer, heparin, vinylpyrrolidone, fibronectin, arginine-glycine-aspartic acid (RGD) containing peptides, or the like, and combinations thereof. A number of surface modifications are known in the art that offer particular advantages for certain uses of the cellulose-based prostheses of the invention. For example, cellulose constructs can be covalently linked to a variety of biomacromolecules, such as cell adhesive peptides, proteins, growth factors, etc. Methods for attachment of biomolecules are known in the art. (See, G. H. M. Engbers, et al., Blood compatible hemodialysis membranes, Trans. Annual meeting of the Society for Biomaterials and the International Biomaterials Symposium, (1994) p. 109; J. Morales et al., Plasma modification of cellulose fibers for composite materials, *J. Appl. Polym. Sci.*, (2006); 101: 3821-3826; J. Zhang et al., Chemical modification of cellulose membranes with sulfoammonium zwitterionic vinyl monomer to improve hemocompatibility, Colloids and Surfaces B: Biointerfaces (2003); 30:249-257; I. K. Ko and H. Iwata, An approach to constructing three-dimensional tissue, *Ann. New York Acad. Sci.*, (2001) 443-455; J. Yuan et al., Improvement of blood compatibility on cellulose membrane surface by grafting betaine, Colloids and Surfaces B: Biointerfaces (2003); 30:147-155) all incorporated herein by reference). U.S. Pat. No. 6,800,753, incorporated herein by reference, describes the preparation of aldehyde-functionalized cellulose scaffolds. Such functionalized hybrid (cellulose-cell) prostheses find particular use in tissue engineered heart valve constructs (in which cellulose can be digested with cellulase in vitro).

The type of cellulose that forms the cellulose-based prosthesis can be derived from any variety of cellulose sources known in the art such as, for example, cotton linters, purified cotton, paper, α-cellulose, purified wood pulp, microcrystalline cellulose, powdered cellulose, cellulose modified to other polymers, and/or similar materials as known in the art, or mixtures thereof (see, e.g., U.S. Pat. Nos. 6,627,749; 6,821,531; and 6,800,753; and Published U.S. Patent Application Nos: 2002/0086990; 2005/0131225; 2005/0287208; and 2006/0093672, each incorporated by reference herein).

Process for Preparing Cellulose-based Heart Valve Prosthesis

In one aspect, the invention provides for methods for preparing a cellulose-based membrane structure comprising (a) providing a source of cellulose; (b) treating the cellulose with paraformaldehyde in anhydrous dimethylsulfoxide (DMSO) under conditions suitable to form methylolcellulose; (c) optionally mixing the methylolcellulose with a water-soluble porogen; (d) casting the methylolcellulose mixture or methylolcellulose and porogen mixture in a mold; (e) soaking the methylolcellulose and porogen in a DMSO-miscible organic solvent or a mixed solvent system (e.g., water/acetone; methanol-2-propanol (2:1)) in which methylolcellulose is not soluble under conditions suitable to form a solid methylolcellulose-porogen matrix; and (f) removing the matrix from the mold and soaking the solid matrix in water until the cellulose-based structure is formed. In embodiments of the above aspect when the method does not comprise (c) the soaking associated with (e) can also be optional in the method.

In one embodiment the method relates to preparing a cellulose-based prosthesis structure formed as a single unit comprising (a) providing a source of cellulose; (b) treating the cellulose with paraformaldehyde in anhydrous dimethylsulfoxide (DMSO) under conditions suitable to form methylolcellulose; (c) optionally mixing the methylolcellulose with a water-soluble porogen; (d) casting the methylolcellulose mixture or methylolcellulose and porogen mixture in a mold; (e) soaking the methylolcellulose and porogen in a DMSO-miscible organic solvent or a mixed solvent system (e.g., water/acetone; methanol-2-propanol (2:1)) in which methylolcellulose is not soluble under conditions suitable to form a solid methylolcellulose-porogen matrix; and (f) removing the matrix from the mold and soaking the solid matrix in water until the cellulose-based structure is formed, wherein the mold comprises the shape of a sheet, a thin film, a hollow tube, or a heart valve. In embodiments of the above aspect when the method does not comprise (c) the soaking associated with (e) can also be optional in the method. In an embodiment, the cellulose-based prosthesis comprises the shape of a heart valve. In further embodiments, the cellulose-based prosthesis comprises the shape of a heart valve selected from an aortic valve, a pulmonary valve, a tricuspid valve, or a mitral valve.

General methods for regenerating cellulose and forming membranes are known in the art (see, e.g., U.S. Pat. No. 6,800,753, incorporated by reference herein). In an embodiment of the above described method, the organic solvent soaking procedure described in (e) was found to result in the precipitation of methylolcellulose, leading to the formation of a solid methylolcellulose-porogen matrix. The organic solvent soaking step produces an improved cellulose-based membrane structure having a more uniform surface pore distribution relative to a membrane prepared using a water soaking step (instead of an organic solvent). In one embodiment of the invention, the organic solvent soaking step (e) is performed for at least about 12 hours or more. One of skill in the art will be able to determine whether the organic solvent soaking step is complete based upon whether the methylolcellulose/porogen mixture has solidified. A "DMSO-miscible organic solvent" as used herein means any organic solvent that is mixable, or soluble, in DMSO without exhibiting significant phase separation. Some non-limiting examples of known DMSO-miscible organic solvents include acetone, acetonitrile, t-butyl alcohol, diethylene glycol, ethanol, ethylene glycol, methanol, propanol, and the like. In one embodiment the organic solvent comprises a DMSO miscible organic solvent such as, for example, acetone.

While particular conditions for forming methylolcellulose can be determined by one of skill in the art, in one embodiment the treating step (b) comprises a temperature range from about 100° C. to about 160° C. In another embodiment, the treating step (b) comprises a temperature range from about 120° C. to about 140° C. (See, e.g., U.S. Pat. No. 6,800,753). In embodiments methylolcellulose solutions are stored under dry conditions.

As mentioned above, any type of cellulose known in the art can be used in the method of the invention.

The porogen used in the method can be any type of water-soluble porogen known to one of skill in the art such as, for example, carbohydrates including lactose, sucrose, galactose, and fructose; and ionic salts including potassium chloride and sodium chloride. One of skill will recognize that the type and the amount of water-soluble porogen can be selected based on the desired physical characteristics of the resulting cellulose matrix material such as, for example, the degree of porosity or the size and shape of the pores. Generally, as particle size of the porogen increases, the resulting pore size also increases. Similarly, increasing in the amount of the porogen can lead to a higher degree of porosity, but this porosity effect can diminish at higher percent weight (porogen/cellulose) compositions One skilled in the art can readily determine an optimal porogen amount for any particular cellulose/porogen combination. See, for example RoyChowdhury & Kumar, "Fabrication and Evaluation of Porous 2,3-Dialdehydecellulose Membrane as Potential Biodegradable Tissue-engineering Scaffold," *J. Biomed. Mater. Res.*, (2006) 76A: 300-309, incorporated by reference.

In yet another aspect, the invention provides for cellulose-based structures produced by the method of the invention. In one embodiment the cellulose-based structure produced by the method of the invention comprises a membrane, a sheet, a hollow tube, a heart valve, or a combination thereof. In one embodiment the cellulose-based structure produced by the method of the invention comprises a single-pieced heart valve prosthesis comprising a plurality of leaflet-forming membranes and a stent body. In another embodiment, the cellulose-based structure produced by the method of the invention comprises a single-pieced aortic heart valve prosthesis comprising a trileaflet structure formed by three leaflet-forming membranes and a stent body, wherein the stent body defines a generally tubular shape centered about an axis; and the trileaflet structure is located within the stent body so as to form a one-way valve prosthesis, wherein the valve prosthesis comprises a proximal end and a distal end.

The following Examples are merely illustrative of certain embodiments of the invention, which is defined by the appended claims. Accordingly, the Examples should not be considered limiting to the scope or spirit of the invention.

EXAMPLES

Example 1

Preparation of Regenerated Cellulose Membranes

A general schematic of one embodiment for preparing porous regenerated cellulose (RC) membranes is illustrated in FIG. 1. Briefly, cellulose (cotton linter) was converted into methylolcellulose by treatment with paraformaldehyde in anhydrous dimethylsulfoxide (DMSO) at 120-140° C. To produce a porous membrane, the resulting highly viscous, opalescent methylolcellulose solution was mixed with a water-soluble porogen (for example, sodium chloride) and cast on a glass plate or in a petri dish. The glass plate/petri dish was then immersed in acetone for 24 hrs. This caused an immediate precipitation of methylolcellulose, forming a solid methylolcellulose-porogen matrix. The matrix was removed from the glass plate/petri-dish and placed in water until a free-floating, porous cellulose membrane is formed. Exposure to water regenerates cellulose from methylolcellulose, concomitant with the dissolution of the water soluble porogen (salt), leading to the formation of a porous prosthesis that is less dense than water. Incorporation of a water immersion initially (i.e., instead of acetone) has produced membranes with non-uniform surface pore distributions.

Example 2

Construction of Heart Valve Prosthesis

Figure 2:
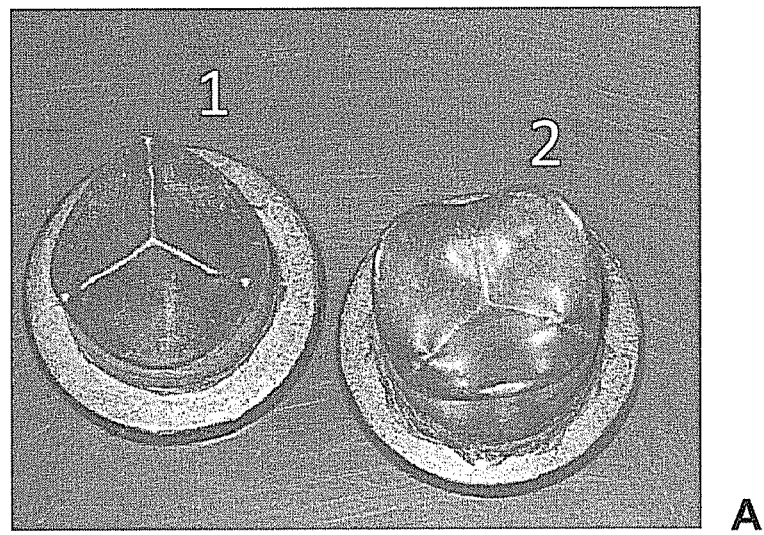
FIG. 2A depicts an embodiment of a mold (or alternatively "casting mold, "casting form," or "casting member") that can be used in the invention. Materials that can be used as a mold include stainless steel, Teflon, or any other material which is resistant to DMSO and does not adhere to cellulose. The molds depicted in this Figure are for generating a cellulose-based trileaflet-stent aortic heart valve prosthesis. The molds are 22 mm in diameter and fit within the hollow high-density polyethylene (HDPE) cylinder, which is 25 mm in diameter (FIG. 2B).
FIG. 2C illustrates the HDPE cylinder-steel mold assembly, with the flanges of the steel molds fitting on the outer edge of the HDPE cylinder. This depicted mold was provided by Dr. Simon P. Hoerstrup (University of Zurich) and is known in the art (see, e.g., Sodian, et al., *Tissue Engineering*, (2000), 6(2):183-188; and Sodian, R., Hoerstrup, S. P., et al., *Ann. Thorac Surg.*, (2000); 70:140-144).
Figure 2:
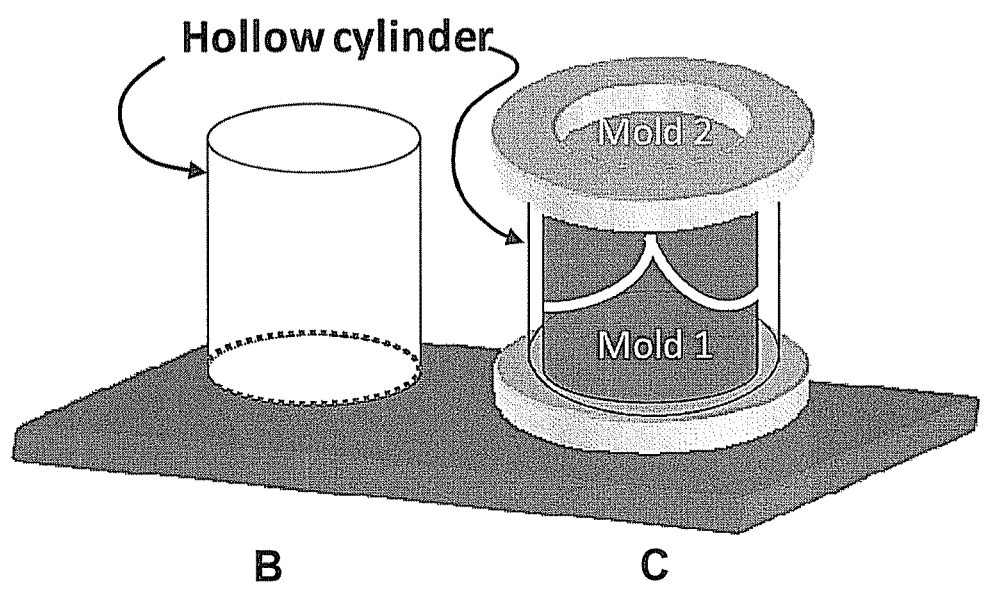

For constructing the porous heart valve prosthesis, a mold and a hollow cylinder pair were used (see, FIG. 2). The hollow cylinder was placed on mold (1). A thoroughly mixed methylolcellulose-NaCl mixture was then filled into the cylinder, ensuring that the mold stayed in the center. Mold (2) was then placed (face-down) on the open end of the cylinder and pushed until the mold's flange touched the edge of the cylinder (FIG. 2C). The whole assembly was placed in acetone for 72-120 hrs. This causes an immediate precipitation of methylolcellulose, forming a solid methylolcellulose-porogen matrix. The acetone soak caused methylolcellulose to precipitate and form a uniform methylolcellulose-NaCl matrix which, in this Example, conformed to the shape of an aortic heart valve.

The solidified methylolcellulose-sodium chloride (NaCl) matrix was removed and placed in water until a porous cellulose heart valve prosthesis was formed. The water was replaced every 12 hrs until it tested negative for chloride ions (by $AgNO_3$ test). The resulting heart valves can be sterilized in 70% ethanol (24-48 hr. at room temperature) and stored in 70% ethanol for an indefinite period of time. FIGS. 3A-3C are photographs of a cellulose-based aortic valve prosthesis prepared by this procedure.

Example 3

Cell Culture on Heart Valve Prosthesis

Myofibroblast cells and endothelial cells, isolated from human saphenous vein and expanded to five or six passages were used to study the cell culture properties of the cellulose based heart valve prosthesis. The cells were provided by Dr. Simon P. Hoerstrup (University of Zurich) and obtained following the general procedure reported by Hoerstrup et al. (*Circulation*, (2000) 102(19):44-49).

Myofibroblast cells were seeded by the conventional dripping method. Briefly, appropriate numbers of myofibroblast cells, equivalent to give $2\times10^6$ cells/cm$^2$ of prosthesis, were suspended in a minimum volume of Advanced DMEM and then dripped onto the distal surface of the valve. Following incubation for 30 min, the proximal end of the prosthesis was seeded with equal number of myofibroblast cells. The valve was incubated again for 30 min and then transferred to a cell culture bottle. Approximately 300 mL of the advanced DMEM (containing 0.25% w/v ascorbic acid plus the other components noted above) was added, and the seeded prosthesis was incubated statically for six weeks. About 60-70% of the medium was replaced with fresh advanced DMEM every fifth day.

After six weeks, endothelial cells (corresponding to $1\times10^6$ cells/cm$^2$ of the prosthesis), expanded to passage four, were seeded in the same manner as described for the myofibroblast cells. The prostheses were incubated in EMB-2 (Cambrex) medium supplemented with 20% (v/v) fetal calf serum and EGM™-2 SingleQuots Kit (CC-4176, Clonetics/Lonza) containing FBS (10 mL), hydrocortisone (0.2 mL), human fibroblast growth factor (hFGF-B) (2 mL), vascular endothelial growth factors (VEGF) (0.5 mL), human recombinant long-insulin-like growth factor-1 ($R^3$-IGF-1) (0.5 mL), ascorbic acid (0.5 mL), hEGF (0.5 mL), gentamycin and amphotericin (GA-1000) (0.5 mL), and heparin (0.5 mL) at 37° C., for 4 days. In total, the prosthesis was cultivated with myofibroblast cells for five weeks and with endothelial cells for 2 weeks. The valves were then cut open vertically to form three equal portions, each portion containing an entire leaflet section and attached stent portion. These portions were separated and analyzed for cellular and extracellular components by three techniques, scanning electron microscopy, biochemical tests, and histological tests.

Tissue Formation Characterization

Figure 4:
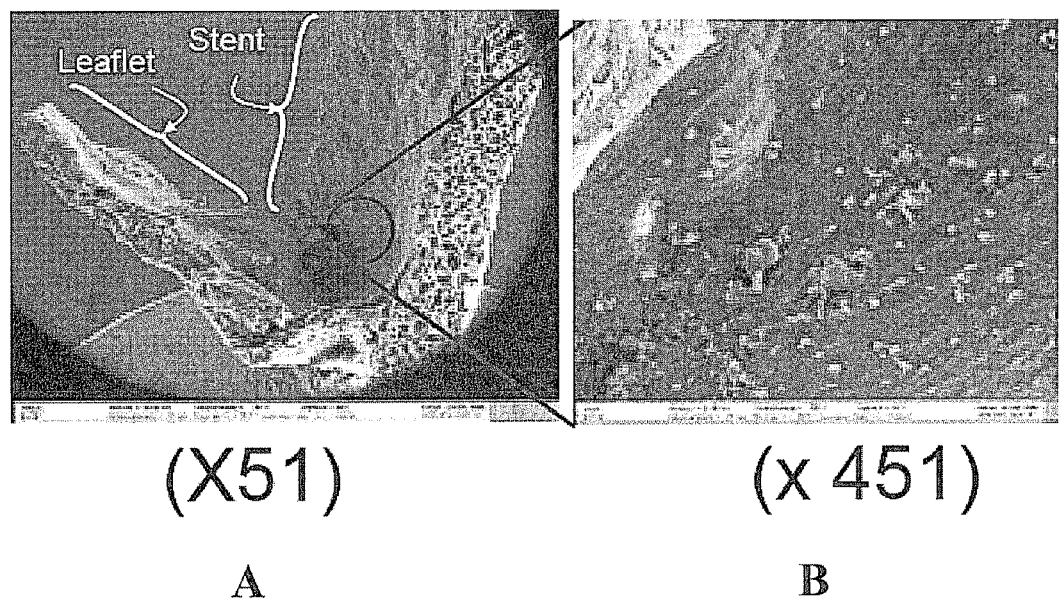
FIG. 4 depicts the scanning electron micrographs (SEM) showing the presence of a thick cellular layer on the leaflet and stent portion of an aortic heart valve prosthesis (magnifications: A×51 and B×451).
Figure 5:
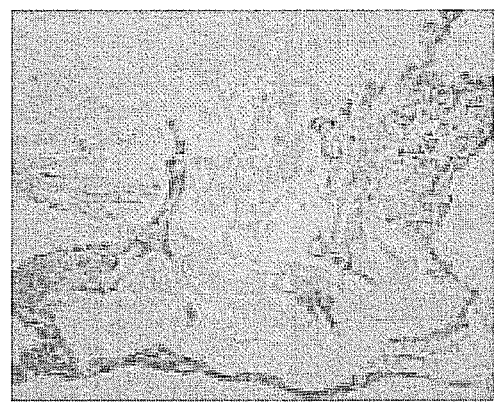
FIG. 5 depicts the hematoxylin and Eosin (H & E) (A & B) and Masson's trichrome stained sections of the leaflet and stent portions of the valve (H & E stains chromatin in blue and cytoplasm in pink; Masson trichrome stains collagen in blue). In this Figure, darker shades of gray indicate positive regions of H & E and Masson trichrome staining.
Figure 5:
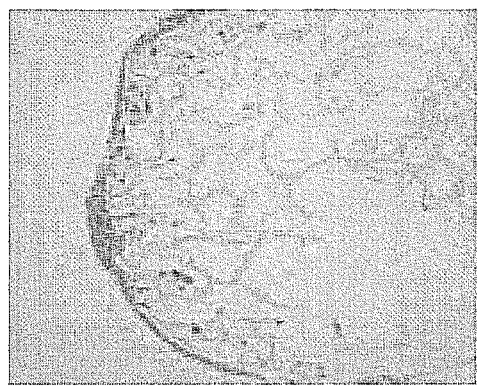
Figure 5:
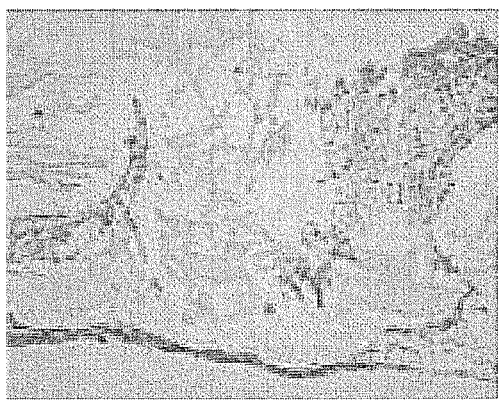
Figure 5:
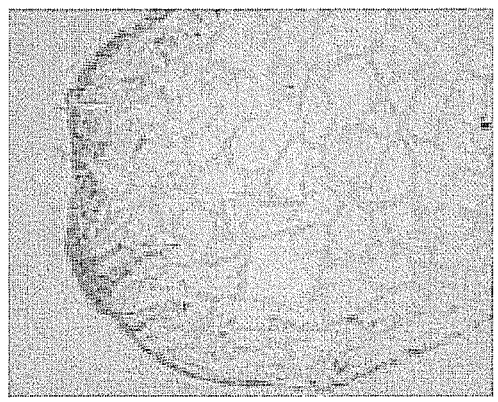

Cell attachment, morphology, and spatial organization were examined by scanning electron microscopy (SEM). The samples were fixed in 2% glutaraldehyde with 0.1 M cacodylate buffer (pH 7.2) for 24 hours at 4° C. Each specimen was washed with buffer and then incubated for an hour at 4° C. in a secondary fixative of 1% osmium tetraoxide in 0.1 M cacodylate buffer. Each specimen was then washed and dehydrated by successive treatment with a series of solutions increasing in ethanol concentration from 20, 40, 60, and 100%, dried by critical point drying with hexamethyldisilazine, sputter coated with gold, and finally viewed with a scanning electron microscope. FIGS. 4 (A and B) shows the micrographs of the prosthesis-cell constructs harvested as described above. As is evident from FIG. 4, a thick cellular layer is present on the prosthesis surfaces. The histology results are presented in FIG. 5. The samples were fixed in 4% phosphate buffered formalin and embedded in paraffin. Thin sections (thickness 5 µm) were cut and stained with hematoxylin and eosin (H & E) (FIGS. 5A & 5B) and Masson's trichrome (MT) (FIGS. 5C and 5D). The presence of purple and blue staining (manifested as darker gray in non-color versions) shows the presence of a cellular lining and extracellular matrix on the prosthesis surfaces. Some cell in-growth in the peripheral region is also evident.

DNA Content

Figure 6:
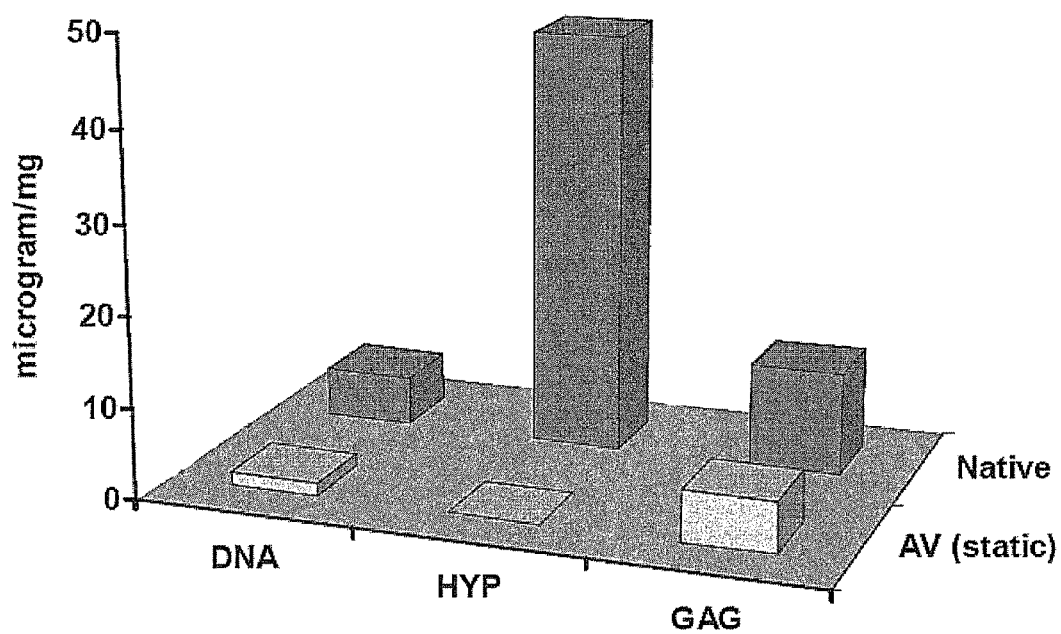
FIG. 6 depicts the amount of DNA, hydroxyproline and sulfated-glycosamine glycans (s-GAGs) present in the bioengineered aortic heart valve prosthesis (AV) relative to native tissue.

The cellular content of the prosthesis was indirectly estimated fluorometrically by measuring the DNA content using Hoechst dye (Bisbenzimide H 33258, Fluka) and the excitation and emission wavelengths of 355 nm and 460 nm, respectively, following the literature procedure (Kim, Y. J., et al., *Anal Biochem*, (1988) 174:168-176). Briefly, the prosthesis was digested using papain solution (125 mg/ml) containing sodium phosphate (pH 6.5; 100 mM), cysteine (5 mM), and EDTA (5 mM) and then treated with Hochest dye. Calf thymus DNA was used as a standard. The DNA contents in the prosthesis and the native tissue as determined are presented in FIG. 6.

Extracellular Matrix Components

Hydroxyproline (HYP) represents the collagen content of the prosthesis. It was determined according to the procedure reported by Huszar et al. (*Anal Biochem*, (1980) 105:424-429). Briefly, an accurately weighed amount (2-4 mg) of the freeze-dried prosthesis was hydrolyzed in 4M NaOH (50-100 µl) in an autoclave at 120° C. for 10 min. The solution was neutralized with 1.4M citric acid. Chloramine-T was then added and the mixture was allowed to stand at room temperature for 25 min. Aldehyde-perchloric acid solution (1M) was subsequently added and the mixture was heated at 65° C. for 15 min. The resulting solution was analyzed spectrophotometrically at 570 nm. The amount of HYP in the sample was calculated from a standard curve constructed using the known amounts of trans-4-hydroxyl-L-proline (Sigma-Aldrich, USA). The results are presented in FIG. 6, which also includes a summary of the sulfated-Glycosamine glycans (sGAGs) contents. The sGAGs were determined calorimetrically using 1,9-dimethylmethylene blue stain, following digestion with papain solution (125 mg/ml) containing sodium phosphate (pH 6.5; 100 mM), cysteine (5 mM), and EDTA (5 mM), according to the procedure of Farndale et al. (*Biochim Biophys Acta*, (1986) 883:173-177. The results show a much lower amount of HYP relative to GAG with respect to the corresponding values for the native, which is likely due to the static cell culture condition used in the study.

Example 4

Mechanical Properties of Cellulose-based Heart Valve Prosthesis

Figure 7:
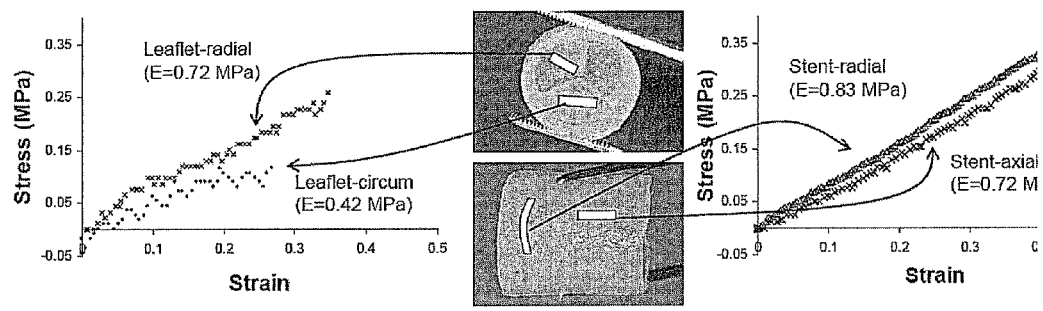
FIG. 7 depicts the design and results from the uniaxial extension testing of prosthesis leaflet and stent specimens. The data points relate to each of the configurations as indicated in the Figure, and are shown for all specimens until the failure point. "E" represents the elastic modulus, which is the best-fit slope of the stress-strain data.

The mechanical characteristics (stiffness, strength, anisotropy etc.) of the unseeded prosthesis material (Example 2) were evaluated under uniaxial extension using an EnduraTec Smart Test System (Minnetonka, Minn.) equipped with a 10 N load cell. Four specimens were cut from the prosthesis (see, FIG. 7): two from leaflets (with one oriented radially and the other circumferentially) and two from the cylindrical stent (with one oriented radially and the other axially). The specimens were held between plate clamps, placed in a specimen bath filled with saline solution and attached to crossheads in the test machine. The specimens were extended at a strain rate of 20% per minute, until failure. The force extension data were converted to stress strain data, from which the elastic modulus was determined as the slope of the best-fit straight line to the elastic portion of the stress-strain curve (see FIG. 7). The elastic moduli for the leaflet portion in the radial and circumferential orientations were 0.72 MPa and 0.42 MPa, respectively. The elastic moduli for the stent portion in the radial and axial orientations were 0.83 MPa and 0.72 MPa, respectively. The moduli for other relevant materials include: non-woven polyglycolic acid (prosthesis material for valve leaflets) 1.3 MPa (radial) and 0.7 (circumferential) (Mol, A., et al., *Circulation*, (2006), 114 (suppl 1):1152-1158); canine aortic valve leaflet, 0.24 MPa (in vivo at systole) (Thubrikar, M., et al., *Circ Res*, (1980), 47(5):792-800); glutaraldehyde-fixed bovine pericardial valve leaflet, 0.2 MPa (low strain) and 20 MPa (high strain) (Zioupos, P., et al., *J Mater Sci:*

*Mater Med*, (1993), 4(6):531-537); and polyurethane leaflet material, 5-60 MPa (Bernacca G. M., et al., *Biomaterials*, (2002), 23(1):45-50).

Hemodynamic Performance.

Figure 8:
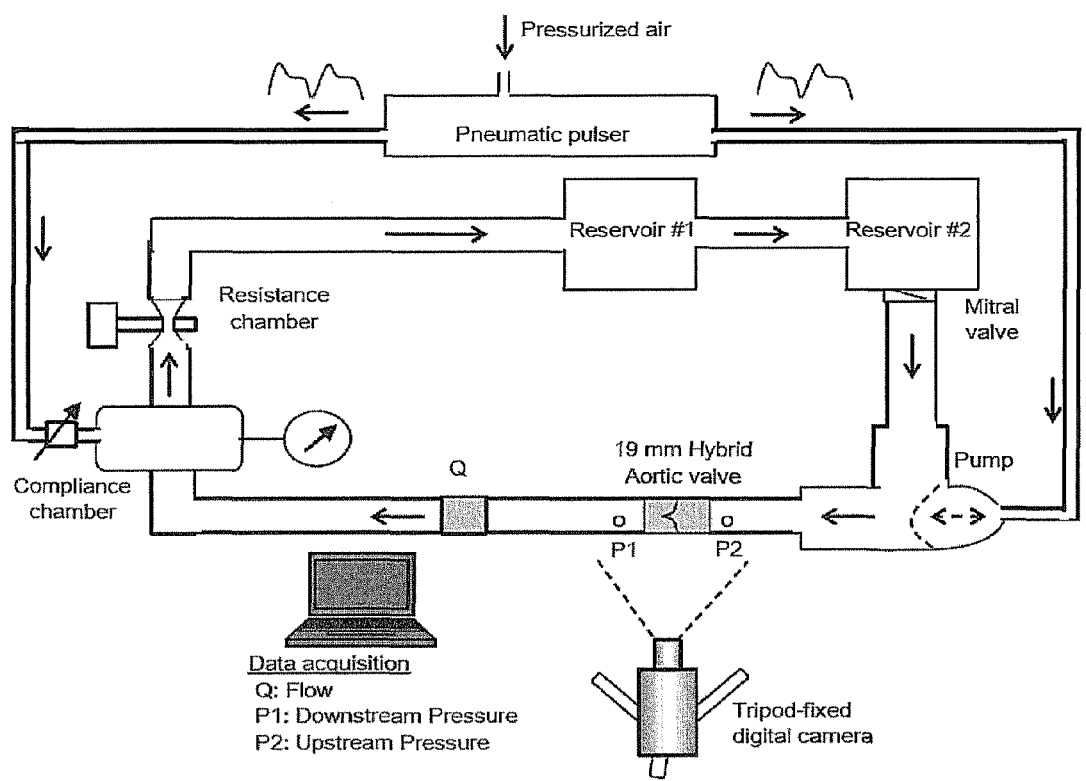
FIG. 8 depicts a schematic illustration of a pulse-duplicating flow loop.

The in vitro hemodynamic performance of the unseeded valve (Example 2) was analyzed using a mock circulatory system that simulates physiological pulsatile flow (Chandran, K. B., et al., *J Biomech*, (1984) 17(8):609). A description of the system follows, and FIG. 8 shows a schematic of the pulse duplicating flow loop. The fluid used in the loop was a 30-40% glycerin to water mixture solution (viscosity 3.5 m Pa s; density 1.13 g/ml). Referring to FIG. 8, the flow loop includes a supply reservoir, a left atrium chamber, a mitral valve chamber equipped with a bileaflet mechanical valve, a pneumatically operated diaphragm pump, an aortic valve chamber in which the unseeded valve is placed, a compliance chamber and a resistance chamber. A pneumatic pulser connected to the diaphragm allows for control of both the rate and strength of the diaphragm motion. The compliance and resistance chambers allow for simulation of the resistance from the peripheral vascular bed in human circulation. By adjusting the compliance and resistance of the system, the pressure pulse waveform and flow rate waveform are controlled to ensure realistic pulse duplicating flow. A Millar flow sensor is installed right after the aortic valve chamber, and an access is available for insertion of Millar pressure catheters (7 Fr SPR-370 tip pressure catheter, Millar Instruments, Houston, Tex.) upstream and downstream to the valve. The flow and pressure sensors are connected to an A/D board attached to a computer where real-time flow and pressure data are acquired at 200 Hz using data acquisition software (Labview; National Instruments, Austin, Tex.). The pneumatic pulser also provides a trigger to the computer, thus allowing for synchronization of flow pulsation and data acquisition. The computer is equipped with custom algorithms that can also perform numerical integration operations to determine valve performance characteristics, such as cardiac output, % regurgitation, and average pressure drop across the valve etc. based on the sensor input.

Figure 9:
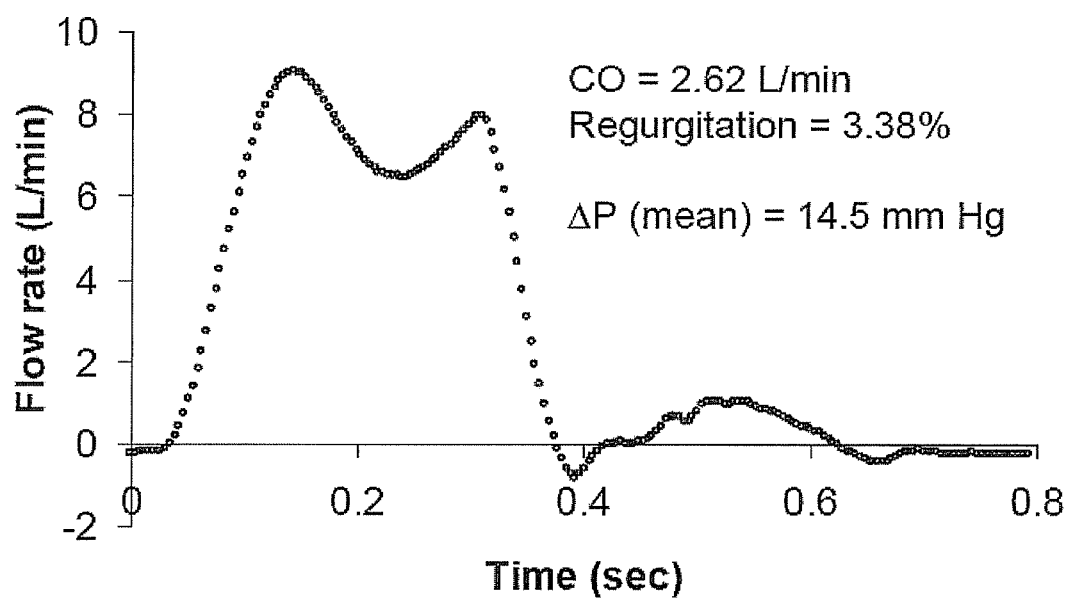
FIG. 9 depicts the measured flow rate waveform of the aortic heart valve prosthesis showing the valve opening, closing, and regurgitation.

An unseeded 19 mm prosthesis valve (pediatric sized) was inserted in a size matching transparent silicone tube and placed in the aortic valve position. The pneumatic pulser, compliance chamber and resistance were adjusted to create a pulse duplicating flow at 75 bpm, 0 to 120 mmHg ventricular pressure and time-averaged flow rates ranging from 2.6 to 4.5 L/min. Flow rate and pressure data were collected for 30 cycles for each time-averaged flow rate and ensemble-averaged. FIG. 9 illustrates the measured flow rate with the prosthesis valve showing valve opening phase, closure and regurgitation. Performance characteristics such as mean and peak pressure drop, cardiac output and percent regurgitation were calculated (FIG. 9). Given that the valve used was pediatric in size, a 2.6 L/min cardiac output is appropriate for assessment. At this cardiac output, the time-averaged pressure drop was 14.5 mmHg, peak pressure-drop was 41.5 mmHg and % regurgitation was 3.38%. The % regurgitation remained below 2% even at higher flow rates of 4.5 L/min.

I claim:

1. A method for preparing a cellulose-based porous structure comprising
    (a) providing a source of cellulose;
    (b) treating the cellulose with paraformaldehyde in anhydrous dimethylsulfoxide (DMSO) under conditions suitable to form methylolcellulose;
    (c) mixing the methylolcellulose with a water-soluble porogen;
    (d) casting the methylolcellulose and porogen mixture in a form; then
    (e) soaking the methylolcellulose and porogen in a DMSO-miscible organic solvent or mixed solvent system under conditions suitable to form a solid methylolcellulose matrix; and then
    (f) removing the matrix from the form and soaking the solid matrix in water until the solid cellulose-based porous structure is formed.

2. The method of claim 1, wherein the porogen comprises potassium chloride, sodium chloride, lactose, sucrose, galactose, fructose, or a mixture thereof.

3. The method of claim 1, wherein the porogen comprises sodium chloride.

4. The method of claim 1, wherein step (e) comprises soaking the methylolcellulose and porogen in acetone for about 12 hours to about 120 hours.

5. A method for preparing a cellulose-based porous heart valve prosthesis formed as a single unit comprising:
    (a) providing a source of cellulose;
    (b) treating the cellulose with paraformaldehyde in anhydrous dimethylsulfoxide (DMSO) under conditions suitable to form methylolcellulose;
    (c) mixing the methylolcellulose with a water-soluble porogen;
    (d) casting the methylolcellulose and porogen mixture in a form; then
    (e) soaking the methylolcellulose matrix in a DMSO-miscible organic solvent or mixed solvent system under conditions suitable to form a solid methylolcellulose matrix; and then
    (f) removing the matrix from the form and soaking the solid matrix in water until the solid cellulose-based porous structure is formed,
wherein the form comprises the shape of a heart valve and stent body.

6. The method of claim 5, wherein the porogen comprises potassium chloride, sodium chloride, lactose, sucrose, galactose, fructose, or a mixture thereof.

7. The method of claim 5, wherein the porogen comprises sodium chloride.

8. The method of claim 5, wherein step (e) comprises soaking in acetone for about 12 hours to about 120 hours.

9. The method of claim 5, further comprising culturing the heart valve prosthesis in cell culture, under conditions that allow for attachment, ingrowth, or propagation of the cell culture on the heart valve prosthesis.

10. The method of claim 9, wherein the cell culture comprises a mammalian cell culture.

11. The method of claim 10, wherein the mammalian cell culture comprises myofibroblast cells or endothelial cells, or both.

12. A method for preparing a cellulose-based heart valve prosthesis formed as a single unit comprising:
    (a) providing a source of cellulose;
    (b) treating the cellulose with paraformaldehyde in anhydrous dimethylsulfoxide (DMSO) under conditions suitable to form methylolcellulose;
    (c) casting the methylolcellulose in an appropriate mold; and
    (d) removing the solidified methylolcelllulose matrix from the mold and soaking the solid matrix in water until the solid cellulose-based heart valve is formed,
wherein the mold comprises the shape of a heart valve and stent body.

* * * * *